(12) United States Patent
Chiappe et al.

(10) Patent No.: US 10,035,971 B2
(45) Date of Patent: Jul. 31, 2018

(54) METHOD FOR TREATING ALGAE

(71) Applicant: STAMICARBON B.V., Sittard (NL)

(72) Inventors: Cinzia Chiappe, Pisa (IT); Christian Pomelli, Pisa (IT); Andrea Mezzetta, Pisa (IT); Barbara Masciocchi, L'Aquila (IT); Alessio Gentile, L'Aquila (IT)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 15/327,358

(22) PCT Filed: May 11, 2015

(86) PCT No.: PCT/EP2015/060309
§ 371 (c)(1),
(2) Date: Jan. 18, 2017

(87) PCT Pub. No.: WO2016/012116
PCT Pub. Date: Jan. 28, 2016

(65) Prior Publication Data
US 2017/0175031 A1    Jun. 22, 2017

(30) Foreign Application Priority Data
Jul. 23, 2014 (EP) .................... 14178212

(51) Int. Cl.
C07C 51/42 (2006.01)
C11B 1/10 (2006.01)
C11B 1/04 (2006.01)

(52) U.S. Cl.
CPC . C11B 1/10 (2013.01); C11B 1/04 (2013.01)

(58) Field of Classification Search
CPC .................................... C11B 1/10; C11B 1/04
USPC ......................................................... 554/204
See application file for complete search history.

(56) References Cited

U.S. PATENT DOCUMENTS

| | | | |
|---|---|---|---|
| 2008/0058549 A1 | 3/2008 | Jessop et al. | |
| 2009/0234146 A1* | 9/2009 | Cooney | B01D 11/0288 554/174 |
| 2011/0076748 A1* | 3/2011 | Salvo | C12N 1/06 435/257.1 |
| 2011/0130551 A1* | 6/2011 | Salvo | C07H 1/08 530/412 |
| 2011/0192792 A1* | 8/2011 | Chew | C12N 1/06 210/633 |
| 2011/0217777 A1* | 9/2011 | Teixeira | C12N 1/12 435/410 |

OTHER PUBLICATIONS

International Search Report for PCT/EP2015/060309, dated Jul. 21, 2015, 4 pages.

* cited by examiner

*Primary Examiner* — Deborah D Carr
(74) *Attorney, Agent, or Firm* — Morrison & Foerster LLP

(57) ABSTRACT

In the present invention a method for treating algae is disclosed, which method comprises the steps of (a) providing an ionic liquid, which is a conjugate of an organic base with $pK_a$ at least 6 and an acid, (b) providing algae, (c) subjecting algae to cell lysis with the ionic liquid, whereby at least two phases are formed, including a hydrophobic phase and a hydrophilic phase, and (d) separating the hydrophobic phase containing lipids.

24 Claims, 3 Drawing Sheets

METHOD FOR TREATING ALGAE

CROSS-REFERENCE TO RELATED APPLICATIONS

Figure 1:
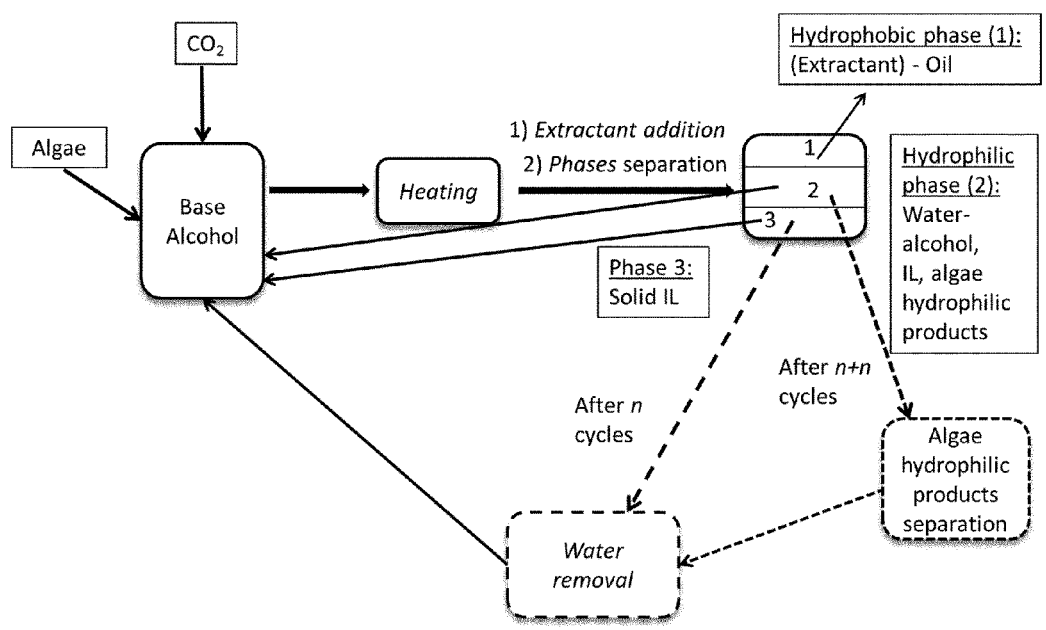

This application is the national phase of PCT application PCT/EP2015/060309 having an international filing date of 11 May 2015, which claims benefit of European patent application No. 14178212.8 filed 23 Jul. 2014. The contents of the above patent applications are incorporated by reference herein in their entirety.

The invention relates to a method for treating algae. Particularly, the invention discloses a method wherein algae are treated using ionic liquid for algae lysis and a lipid-containing phase is separated that is useful in the biofuels production.

BACKGROUND OF THE INVENTION

Algae have been recognized as a potential source for 'green' fuels, in particular biodiesel. Algae are not typically used as food products but can be easily produced in large quantities and have therefore attracted attention for their potential use as fuels. A problem associated with harvesting the valuable oils present in the algae is the energy consumption associated with removing the excess water and the breaking (lysis) of the cell walls to extract the oils. Many mechanical processes for cell wall destruction are known such as centrifugation, mechanical pressure, often combined with elevated temperatures. A relatively recent method uses ionic liquids to effectively dissolve the cells walls thereby releasing the oils within the cells. However, also here the majority of the water needs to be removed to provide the desired ionic liquid strength.

Ionic liquids however are often quite expensive and difficult to produce and are difficult to separate from the reaction mixture and thus hard to recycle. Another problem is that often emulsions are formed which are very difficult to break which makes it difficult to separate the water phase from the oil phase. This problem occurs in particular at higher levels of water (i.e. lower concentration of algae).

It is desired to provide a method for treating algae, which is economical and does not have the herein-above mentioned disadvantages. It is desired that the method allows easy separation of different phases and efficient recycling of the ionic liquid. It is also desired that the method can be applied to wet algae and be effective even at high water content.

SUMMARY OF THE INVENTION

In order to better address one or more of the foregoing desires, the invention presents, in one aspect, a method for treating algae, comprising:

(a) providing an ionic liquid, which is a conjugate of an organic base with $pK_a$ at least 6 and an acid,
(b) providing algae,
(c) subjecting algae to cell lysis with the ionic liquid, whereby at least two phases are formed, including a hydrophobic phase and a hydrophilic phase, and
(d) separating the hydrophobic phase containing lipids.

DETAILED DESCRIPTION OF THE INVENTION

The present invention describes a process for direct oil extraction from algae, preferably, from wet algae, using a particular type of ionic liquids.

The present invention is based on the judicial insight that the problems mentioned herein-above can be at least party overcome by using a particular class of ionic liquids as described below. These ionic liquids are easy to produce (including in situ), are effective as to algal cell lysis also at high water contents and are also easy to recycle. Furthermore, the ionic liquids used in the present invention provide easy separation of the water and product phase, whereby no emulsion is formed, and provide a high oil extraction efficiency. As a further important advantage relevant for biofuels, these ionic liquids allow in situ transesterification with alcohols in order to produce fatty acid methyl esters which are the desired products for biofuel.

The method according to the invention starts with providing an ionic liquid and algae.

The term "ionic liquid" is known to a person skilled in the art. Generally, it means a salt in the liquid state. Particularly, in the context of the invention, "ionic liquids" are salts whose melting point is below 100° C.

The ionic liquids used in the present invention are conjugates of an acid and a base. Typically the conjugate acid/base ionic liquid is obtained by combination of an acid (H-A) with an organic base (B), which is a reversible reaction:

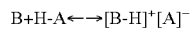

The reaction is a typical acid-base equilibrium. By appropriate selection of $pK_a$ values of the acid and the base, the equilibrium may be shifted more to the conjugate or to the free acid and base.

Such conjugates (also called Brønsted acidic ionic liquids) contain a hydrogen with acidic properties. Brønsted acidic ionic liquids used in the present invention are preferably obtained from a base containing a heteroatom (preferably, nitrogen), which can be protonated when forming the conjugate and deprotonated in the free base form.

It is known to prepare ionic liquids by alkylation of heteroatoms (particularly, nitrogen atoms) of heterocycles through a substitution reaction, which is a non-reversible reaction and transform the base into an onium salt. Examples of such ionic liquids are 1-butyl-3-methylimidazolium chloride ([BMIM]Cl) and 1-ethyl-3-methylimidazolium chloride ([EMIM]Cl). These ionic liquids do not contain protonated nitrogen atoms and are not Brønsted acidic ionic liquids. In water they are neutral salts. These ionic liquids are also not considered conjugates in the present specification as they cannot reversibly dissociate into an acid and a base.

For being useful in the present invention, the unconjugated base should have a sufficient basicity to impede deprotonation to a significant degree by the anion.

The ionic liquid to be used is formed from a strong organic base and an acid. A strong organic base is defined here as having a $pK_a$ of at least 6, in water. The $pK_a$ values mentioned in the present specification preferably relate to the hydrogen atom attached to the heteroatom (more preferably, to nitrogen) and not to carbon that some e.g. dialkylimidazolium salts may contain. $pK_a$ is determined by conventional methods known to a skilled person, e.g. by titration. Preferably, the base in the conjugated form contains a protonated heteroatom, more preferably a protonated nitrogen atom. More preferably, the base is a nitrogen-containing organic base. In some embodiments, the base contains a heterocycle, preferably a nitrogen-containing heterocycle. In other forms, the base is an amine. Examples of suitable bases include tertiary amines such as trialkyl amines, amidines, guanidines, triethylenediamine (dabco), pyridines, pyrimidines, phosphoranes and derivatives thereof. Particularly preferred are triethylamine, 1,1,3,3-tetramethylguanidine (TMG), 1,1,2,3,3-pentaalkylguanidine (PAG), 1,8-diazabicyclo[5.4.0]undec-7-ene (DBU), 1,2-dimethyl-1,4,5,6-tetrahydxopyrimidine or imino-tris(dimethylamino)phosphorane and derivatives thereof.

In some embodiments, the base has a $pK_a$ in the range 6-13. In such embodiments, the ionic liquids are preferably made of a strong acid and a tertiary amine with the above $pK_a$. Strong acids completely ionize in an aqueous solution, they have $pK_a<1$. As the tertiary amine, particularly, the following are suitable: pyridines, N-alkylimidazole, triethylenediamine (dabco), tri-alkylamines, N-alkyl-dabco, N-alkylpyrrolidine, tetraalkylguanidine, DBU and derivatives thereof. Preferred strong acid is sulfuric acid.

In other embodiments, the $pK_a$ of the base is higher than 13. Alternatively formulated, the $pK_a$ of the base is higher than that of tetramethylguanidine (TMG) in the same solvent. The $pK_a$ of TMG in DMSO is 13.6 and in THF 17. In such embodiments, the acid used to form the ionic liquid is preferably a weak acid. Weak acids do not completely ionize in an aqueous solution. Weak acids have a $pK_a$ of more than 1. A particularly preferred acid in this embodiment is carbonic acid.

In general, the acid to be used to form the ionic liquid may be organic or inorganic. Examples of suitable acids include carboxylic acids such as oxalic acid, acetic acid or other longer chains acids, sulfuric acid, hydrochloric acid, methylcarbonic (or other alkylcarbonic) acids, carbonic acid and derivatives thereof.

Ionic liquids obtained with carbonic acid, substituted carbonic acid (particularly alkylcarbonic) and derivatives thereof represent a special embodiment of the present invention because they can be easily recovered by $CO_2$ stripping procedures.

Preferred bases, which are particularly suitable to be used with these anions, are amidines (for example, 1,8-diazabicycloundecene, DBU) and guanidines (for example, tetramethylguanidine, TMG). Examples of such ionic liquids include DBU methylcarbonate (DBUH$^+$ MeOCO$_2^-$), DBU bicarbonate (DBUH$^+$ HCO$_3^-$), TMG methylcarbonate (TMGH$^+$ MeOCO$_2^-$), TMG bicarbonate (TMGH$^+$ HCO$_3^-$). DBU and TMG are neutral organic bases with high proton affinity ($pK_{aDBu}$=25.5 and $pK_{aTMG}$=23.3)

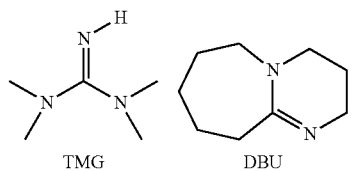

TMG            DBU

In the presence of alcohol (for example, methanol) or water, and $CO_2$, these bases form ILs, i.e. BH$^+$ methylcarbonates or BH$^+$ bicarbonates.

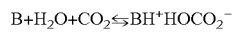

In general, some examples of suitable bases for the ionic liquids used in the present invention are reported in Table 1.

TABLE 1

| Base | Structural formula | $pK_a$ water | $pK_a$ other solvent |
|---|---|---|---|
| 2-methylpyridine | | 6.0 | |
| triethylamine | Et$_3$NH$^+$ | 10.8 | |
| N-methylpyrrolidine | | 10.5 | |
| Dabco | | 8.8 | |
| Quinuclidine | | 11 | |
| Tetramethylguanidine (TMG) | | 15.2 | 13.6(DMSO) 17 (THF) |

TABLE 1-continued

| Base | Structural formula | pK$_a$ water | pK$_a$ other solvent |
|---|---|---|---|
| 1,8-diazabicyclo-[5.4.0]undec-7-ene (DBU) | | | 24.3 (Acetonitrile) |
| 1,5,7-Triazabicyclo[4.4.0]dec-5-ene(TBD) | | | 21.7 (THF) |
| imino-tris-(dimethylamino)-phosphorane | | | 27.9 (THF) |

Algae are preferably provided in the form of a wet algal biomass, which is a water suspension. In a preferred embodiment, the water content in the water suspension is at least 50 wt. %, more preferably 75-90 wt. %. This is an advantage of the present method, which can be applied directly to harvested biomass (optionally after some concentration) and which does not require complete dewatering and drying of the biomass, which may consume a lot of energy. Any suitable type of algae can be used.

In a further step, algae are subjected to cell lysis with the ionic liquid. This can take place, for example, in a lysis reactor. In one embodiment, the algae together or separately with the ionic liquid are introduced in a lysis reactor. In another embodiment, the ionic liquid is formed in situ, e.g. in the lysis reactor, from a respective base and an acid. This is particularly convenient if the acid in the ionic liquid is carbonic acid; the conjugate can then be generated in situ by addition of a gaseous $CO_2$ to the base.

In a preferred embodiment, an organic solvent, preferably, an alcohol, and more preferably methanol or ethanol, can be added to the mixture of the ionic liquid and the algae. Organic solvents can in this way reduce the viscosity, on one hand, and on the other hand act as (trans)esterification agents, that is, they favor fatty acid esters formation. Fatty acids methyl esters (or other alcohol esters) can be directly formed during the lysis process. The preferred organic solvent is methanol as it results in fatty acid methyl esters, which is favourable for the use in biofuel. The use of methanol can lead to a transesterification yield higher than 90%, in combination with the ionic liquids used in the present invention. Conventional ionic liquids such as [BMIM]Cl do not achieve such high transesterification yields as seen in Example 9 below.

The ratio of the conjugated ionic liquid to algae suspension, which can be used, depends on the base. In the absence of alcohol, the mass ratio of the conjugated ionic liquid to cell suspension is preferably in the range of 5:1 to 3:1 (calculated based on the water content of the cell suspension 85 wt. %). In the presence of methanol, the mass ratio of conjugate acid to cells suspension (water content 85 wt. %) is preferably in the range of 7:1 to 3:1 and the mass ratio of alcohol to cell suspension (containing about 85 wt. % of water) is in the range of 2:1 to 0.5:1.

Preferably, the cell lysis is performed at temperatures of 100° C., or less (generally about 80° C.). Preferably, a closed apparatus is used, optionally, under $CO_2$ pressure. The duration of the cell lysis should be sufficient to effect lysis but is generally less than 60 min.

As a result of the cell lysis, at least two phases are formed, including a hydrophobic phase and a hydrophilic phase. These phases are substantially immiscible. The hydrophilic phase mainly contains water, the ionic liquid, alcohol (if used) and hydrophilic algae components (glycerol, water soluble proteins, carbohydrates and metabolites). The hydrophobic phase mainly contains fatty acids and their glycerol esters, waxes and, optionally, the extractant (if used). Optionally, a solid phase is additionally formed as a third phase. This solids phase may for example contain a part of ionic liquid in the form of a precipitate, which is undissolved at the lysis or separation temperature.

Subsequently, the hydrophobic phase is separated by physical separation methods such as decanting, centrifugation, etc. The hydrophobic phase has generally a lower density than the hydrophilic phase is therefore the present as the upper layer. The upper hydrophobic layer can be recovered by mechanical separation or spilling. The two or three phases may be allowed to separate using the forces of gravity or separation might be accelerated, for example by centrifugation. The precipitated ionic liquid can be filtered off and reused in the step of algal cell lysis.

Once the lipid-containing hydrophobic layer is separated from the mixture, the hydrophilic phase containing the ionic liquid, water, hydrophilic algae components and optionally alcohol can be recovered for reuse in the step of algal cell lysis. The phases separation and oil recovery can be favored by temperature reduction, preferably at room temperature or lower, and by the addition of an extractant. Any known extractant for this purpose can be used. Preferably, hexane is used as an extractant.

If desired, algae metabolites or other algae products can be isolated from the hydrophilic phase. This can be done by extraction with organic solvents. The hydrophilic phase can be subsequently reused in the lysis step of the process. Another suitable method to isolate algae metabolites or other algae by-products (carbohydrates and protein) is to remove water, alcohol and the ionic liquid by distillation (the ionic liquid distills as free acid and free base). The ionic liquid can then be reformed from the recovered base and acid, without reduction in yield and degradation in quality, and the resulting ionic liquid can be reused in the cell lysis step.

If the ionic liquid contains carbonate or similar (e.g. bicarbonate, methylcarbonate or alkyl carbonate) as a counter-ion, algae metabolites or other algae by-products (carbohydrates and proteins) can be isolated from the hydrophilic phase by removing water, alcohol and the ionic liquid by heating in a $N_2$ stream, at a temperature lower than 150° C. The ionic liquid can then be formed from the recovered base and acid, and reused in the cell lysis step.

One of the advantages of using the ionic liquids as described above is that Brønsted acidic ionic liquids are easily distilled because they are in equilibrium with the corresponding neutral species (free acid and free base). Free acids and free bases are distilled at a significantly lower boiling point that neutral salt ionic liquids. For comparison, distillation of [BMIM]Cl is impossible. Additionally, an advantage of using carbonic acid or a derivative thereof (e.g. bicarbonate, methylcarbonate or alkyl carbonate) in the ionic liquid is that its counterion can always be recovered by distillation of the components or by $CO_2$ stripping procedures.

The ionic liquid obtained in the separation steps is preferably reused in the step of algal cell lysis. Without any purification or water removal, the lower phases (solid ionic liquid and hydrophilic phase) could be reused at least three times. If algae cell-derived components are recovered from the hydrophilic phase, this phase can be reused in the lysis step for at least 10 cycles.

The ability of the ionic liquid to affect cells lysis depends on the water amount: increasing the water amount decreases the lysis efficiency. Therefore, when desired, e.g. after a certain number of cycles, water can be removed from the ionic liquid obtained in the separation steps. This can suitably be done by heating or reverse osmosis.

It was observed by the inventors that during the use of the described ionic liquids the formation of emulsions was significantly lower than using neutral ionic liquids such as [BMIM]$^+$Cl$^-$. This is a considerable advantage as emulsions are generally difficult to separate or need additional steps or ingredients to allow the separation. Without wishing to be bound by any particular theory, the inventors believe that the presence of a hydrogen atom instead of an alkyl chain on the heteroatom may reduce the surfactant ability of the ionic liquids. In case of the ionic liquids with (substituted) carbonic acid, it is believed that an additional effect is that glycerol (that may be present in the reaction mixture and which is an emulsifier) is removed from the mixture through the formation of another ionic liquid having carbonate glycerol as counter-anion. The removal of glycerol from the reaction mixture is also believed to favour transesterification and easy recycle of the ionic liquids used in the present to the invention.

The ionic liquid used in the present invention offers considerable advantages compared to conventional reagents. Particularly, the above-described ionic liquids are efficient media for algae cell lysis in the presence of high amounts of water (up to 90%). It is possible to obtain an in situ transformation of the fatty acids and their glycerol esters into the corresponding short alcohol esters (such as methyl esters >90%). The used ionic liquids avoid emulsion formation and thus provide for easy phase separation. It is further possible to have a high oil extraction yield (>80%). The ionic liquids can be efficiently recycled, compared to conventionally used solvents (molecular or ionic) for algae processing. Particularly, the described ionic liquids can be recovered by distillation. The purity of the recovered product is an important advantage associated with distillation. The ionic liquids can thus often be reused without substantially compromising the quality of the reagent, which makes the process economic.

A particular advantage of using ionic liquids with carbonic acids is that they can additionally be recovered by $CO_2$ stripping procedures. The purity of the recovered product is an important advantage associated to the use of this type of ionic liquids.

The invention further provides the use of the ionic liquids as described above for the lysis of algae.

Several preferred embodiments are further described with reference to FIGS. 1 and 3.

In FIG. 1, algae are combined with a base, an alcohol and $CO_2$ in a lysis reactor. The ionic liquid (IL) is formed in situ from the base and $CO_2$ in the presence of water (carbonic acid). The alcohol is used for (trans)esterification. The mixture is heated to a suitable temperature to affect the algal cell lysis. After the lysis, optionally an extractant is added to facilitate the phase separation, and phase separation takes place. The obtained mixture generally comprises at the top a hydrophobic phase (1), comprising oil with the optional extractant. The middle phase (2) is a hydrophilic phase containing water-alcohol mixture, the ionic liquid and algae hydrophilic products. The phase at the bottom (3) is the precipitate containing the solid ionic liquid. The phases are separated by conventional separation techniques. Phases (2) and (3) can directly be used in the lysis reactor. If necessary, after a number of cycles, the ionic liquid can be recovered from phases (2) and (3). In that case, phase (3) can be subjected to water removal after n cycles. Phase (2) can be subjected to the removal of algae hydrophilic products and water removal, e.g. after n+n cycles.

Figure 3:
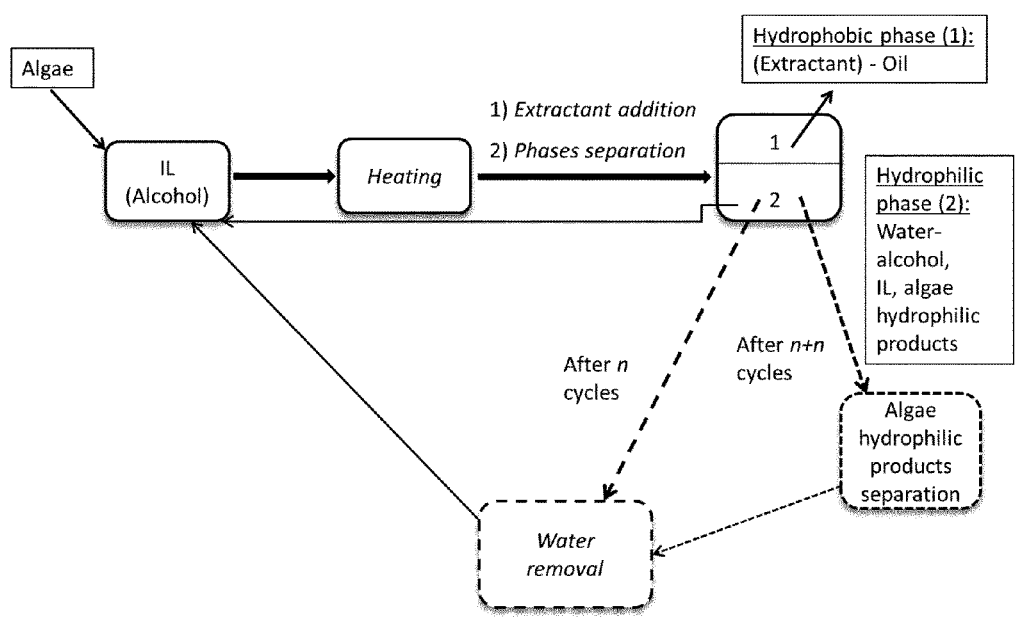

In FIG. 3, algae are combined with the ionic liquid IL (base and acid) and optionally with an alcohol. The mixture is heated to a suitable temperature to affect the algal cell lysis. After the lysis, optionally an extractant is added to facilitate the phase separation, and phase separation takes place. The obtained mixture can comprise two phases: at the top a hydrophobic phase (1), comprising oil with the optional extractant. At the bottom, a hydrophilic phase (2) containing a water-alcohol mixture, the ionic liquid (IL) and algae hydrophilic products. The phases are separated by conventional separation techniques. Phase (2) can directly be used in the lysis reactor. If necessary, after a number of cycles, the ionic liquid can be recovered from phase (2) by water removal, e.g., after n cycles and, additionally, by removal of algae hydrophilic products, e.g. after n+n cycles.

For the purpose of clarity and a concise description features are described herein as part of the same or separate embodiments, however, it will be appreciated that the scope of the invention may include embodiments having combinations of all or some of the features described. The invention will now be illustrated in the following, non-limiting examples. Parts and percentages mentioned in the examples and through the description, are by weight, unless otherwise indicated.

EXAMPLE 1

TMG:$CO_2$:Methanol

The wet algae (5 g, water content around 85%) were added to a mixture of tetramethylguanidine (19 g) and methanol (10 g) in a closed vessel and $CO_2$ was added. Cell lysis was performed at 100° C. for 1 h. Hexane was added to favor oil separation. After centrifugation, a three phase system was obtained: an upper hydrophobic layer, containing the oil; a lower phase (solid), due to the precipitated ionic liquid conjugate (ca. 60% of the starting material), and a middle phase, containing water/methanol+conjugate acid+ the cell lysis hydrophilic products.

The lower phases (solid ionic liquid and hydrophilic phase) could be reused without any purification or water removal at least three times. Subsequently, it was necessary to remove water and algae by-products. The process scheme is shown in FIG. 1.

Figure 2:
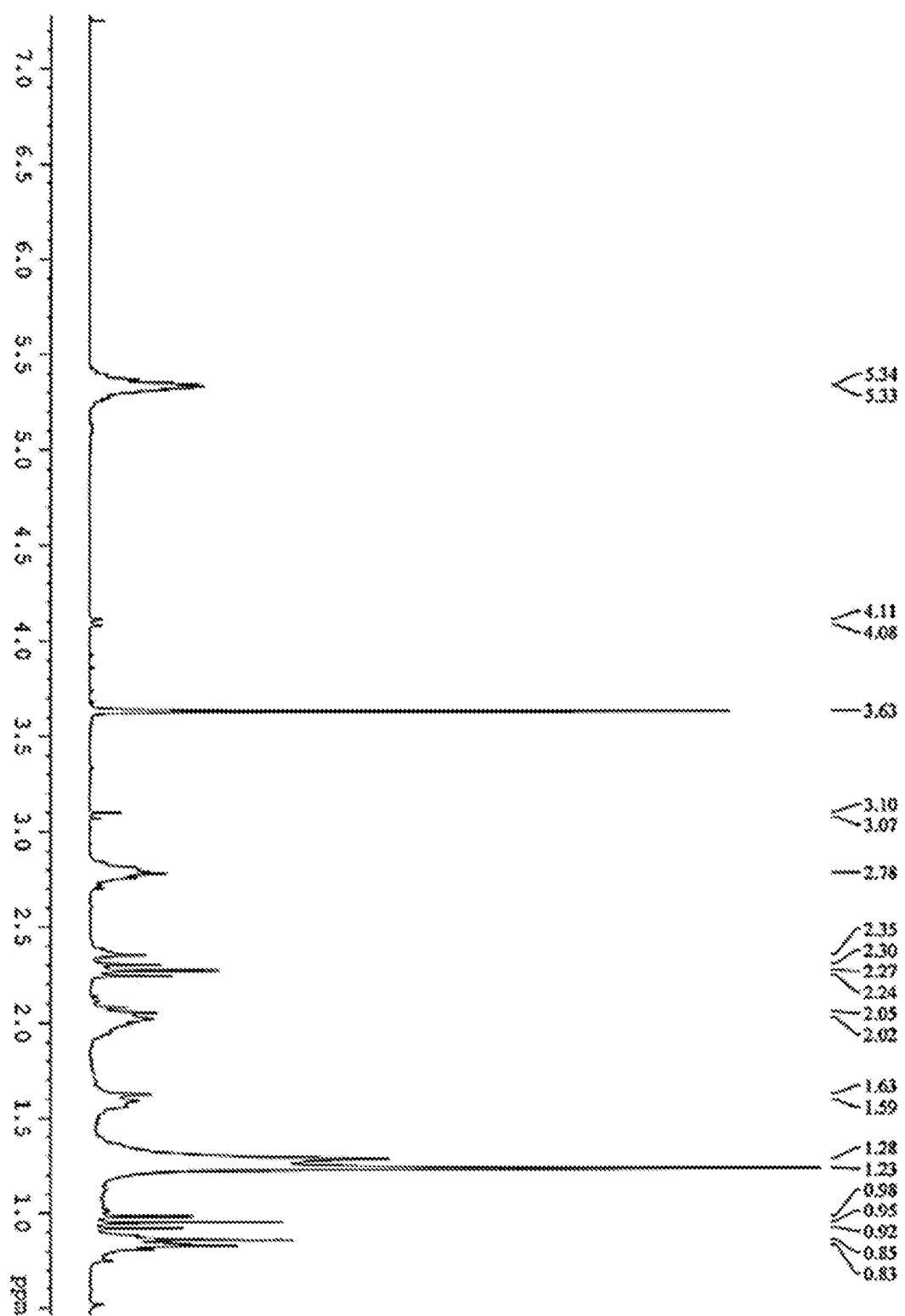

The recovered oil (83% of the total algal oil content) was analyzed by 1H NMR and ESI-MS. The NMR analysis shows almost complete transformation into the corresponding fatty acid methyl esters, ca. 95% (FIG. 2).

EXAMPLE 2

DBU:$CO_2$:Methanol

The wet algae (5 g, water content 85%) were added to a mixture of DBU (25 g) and methanol (7.5 g) in a closed vessel. $CO_2$ was added under pressure. Cell lysis was performed at 100° C. for 1 h. At the end of the experiment, hexane was added to favor oil separation. After centrifugation, a two phase system was obtained: an upper hydrophobic layer, containing the oil; a lower phase, containing water, the ionic liquid and the hydrophilic algae products. The lower phase could be recycled at least three times, without any purification or water removal. After three times, it was necessary to remove water from the lower phase before reuse and algae byproducts.

The recovered oil (65% of the total algal oil content) was analyzed by 1H NMR: the NMR analysis shows almost complete transformation into the corresponding fatty acid methyl esters, 95%.

EXAMPLE 3

TMG Hydrogen Sulphate

The wet algae (5 gr, water content 85%) were added to tetramethylguanidinium hydrogen sulfate (15 gr). Cell lysis was performed at 80° C. for 1 h. At the end of the experiment, hexane was added to favor oil separation. The hydrophobic phase, after hexane evaporation, was analyzed by NMR and GC-MS. The hydrophilic phase could be directly recycled at least three times, without the necessity to remove water.

EXAMPLE 4

TMG Hydrogen Sulphate:Methanol

The wet algae (5 g, water content 85%) and methanol (2.5 g) were added to tetramethylguanidinium hydrogensulfate. Cell lysis was performed at 80° C. for 1 h. At the end of the experiment, hexane (5 ml) was added to favor oil separation and the eventual precipitation of the conjugate acid. After separation of the hydrophobic layer, hydrophilic phase could be recycled three times without water removal. After hexane evaporation, the recovered products were analyzed by NMR and GC.

The recovered oil (75% of the total algal oil content) contained fatty acid methyl esters (ca. 60%). FIG. 3 shows the process scheme.

EXAMPLE 5

[BMIM]Cl:Methanol

The wet algae (5 g, water content 85%) and methanol (8 g) were added to 1-methyl-3-butylimidazolium chloride, [BMIM]Cl (25 gr). Cell lysis was performed at 80° C. for 1 h. At the end of the experiment, hexane (5 ml) was added to favor oil separation. The immediately formed solid was separated by centrifugation whereas the liquid phase, being practically an emulsion, required the addition of relevant amounts of NaCl and several cycles of hexane addition and centrifugation to guarantee oil extraction. The formation of emulsions increased when algae cell lysis was performed with [BMIM]Cl in the absence of methanol.

After separation of the hydrophobic layer, the added inorganic salts and water were removed by centrifugation and distillation, and the recovered liquid was again used for algae extraction. After hexane evaporation, the recovered products were analyzed by NMR and GC.

The recovered oil (60-75% of the total algal oil content) contained mainly fatty acids. This means a significantly lower ability of [BMIM]Cl in methanol to achieve transesterification than the IL's used in Examples 1 and 2 according to the invention.

EXAMPLE 6

[BMIM]Cl

The wet algae (5 g, water content 85%) were added to 1-methyl-3-butylimidazolium chloride, [BMIM]Cl (25 gr). Cell lysis was performed at 80° C. for 1 h. At the end of the experiment, methanol (25 ml) and hexane (5 ml) was added to favor oil separation. The immediately formed solid was separated by centrifugation whereas the liquid phase, practically an emulsion, required the addition of relevant amounts of NaCl and subsequent cycles of hexane addition and centrifugation to guarantee oil extraction. After separation of the hydrophobic layer, the added inorganic salts and water were removed by centrifugation and distillation, and the recovered liquid was again used for algae extraction. After hexane evaporation, the recovered products were analyzed by NMR and GC.

The recovered oil (40-60% of the total algal oil content) contained mainly fatty acids.

EXAMPLE 7

[EMIM] Ethyl Sulfate

The wet algae (5 g, water content 85%) were added to 1-ethyl-3-methylimidazolium ethyl sulfate (25 gr). Cell lysis was performed at 80° C. for 1 h. At the end of the experiment, hexane (5 ml) was added to favor oil separation. The immediately formed solid was separated by centrifugation whereas the liquid phase, practically an emulsion, was centrifuged to favor phase separation and oil extraction. After separation of the hydrophobic layer, water was removed from the aqueous phase and the recovered liquid was again used for algae extraction. After hexane evaporation, the recovered products were analyzed by NMR and GC.

The recovered oil (50-52% of the total algal oil content) contained mainly fatty acids.

EXAMPLE 8

[BMIM] Acetate

The wet algae (5 g, water content 85%) were added to 1-butyl-3-methylimidazolium acetate (25 gr). Cell lysis was performed at 80° C. for 1 h. At the end of the experiment, hexane (5 ml) was added to favor oil separation. The immediately formed solid was separated by centrifugation whereas the liquid phase, practically an emulsion, was centrifuged to favor phase separation and oil extraction. After hexane evaporation, the recovered products were analyzed by NMR and GC.

The recovered oil (40% of the total algal oil content) contained mainly fatty acids.

EXAMPLE 9

Additional experiments were carried out according to the procedure described in Example 1, which are summarized in the following table.

|  | [TMG H]+ [MeOCO$_2$]−/ [HOCO$_2$]− | [DBUH]+ [MeOCO$_2$]−/ [HOCO$_2$]− | [BMIM]Cl/ CH$_3$OH | [BMIM]Cl |
|---|---|---|---|---|
| Oil extraction (%) with respect the total algal oil content | 83 | 68 | 60-75 | 40-60 |
| Transesterification (%) | 95 | 95 | 20 | — |
| Temperature/ Pressure | 100° C./ 10 atm | 100° C./ 10 atm | 100° C. | 100° C. |
| IL/Algae/MeOH | 5:1:1.5 | 5:1:1.5 | 5:1:1.5 | 5:1 |
| Recycle | Very easy | Easy | Difficult | Difficult |
| Emulsion formation | No | No | Yes | Yes Extraction is very difficult |
| IL recovery | Very easy | Easy | Difficult | Difficult |

As shown in the above table, the ionic liquids used in the method according to the invention allow to achieve a high oil extraction, high degree of transesterification when using methanol. The ionic liquids can be easily recovered and recycled and do not show emulsion formation, when compared to [BMIM]Cl, conventionally used in the art.

The invention claimed is:

1. Method for treating algae, comprising:
   (a) providing an ionic liquid, which is a conjugate of an organic base with pK$_a$ at least 6 and an acid,
   (b) providing algae,
   (c) subjecting algae to cell lysis with the ionic liquid, whereby at least two phases are formed, including a hydrophobic phase and a hydrophilic phase, and
   (d) separating the hydrophobic phase containing lipids; wherein the ionic liquid is a Brønsted acidic ionic liquid and contains a hydrogen with acidic properties.

2. The method according to claim 1, wherein the ionic liquid is formed in situ from a respective base and a respective acid.

3. The method according to claim 1, wherein the algae are provided in the form of a water suspension with water content at least 50 wt. %.

4. The method according to claim 1, wherein the base is selected from a list consisting of trialkyl amines, amidines, guanidines, triethylenediamine, pyridines, pyrimidines, phosphoranes and derivatives thereof.

5. The method according to claim 1, wherein the acid is selected from the group consisting of carboxylic acids, sulfuric acid, hydrochloric acid, alkylcarbonic acids, carbonic acid and derivatives thereof.

6. Method for treating algae, comprising:
   (a) providing an ionic liquid, which is a conjugate of an organic base with pK$_a$ at least 6 and an acid,
   (b) providing algae,
   (c) subjecting algae to cell lysis with the ionic liquid, whereby at least two phases are formed, including a hydrophobic phase and a hydrophilic phase, and
   (d) separating the hydrophobic phase containing lipids; wherein the base has a pK$_a$ in the range 6-13 and the acid has a pK$_a$ less than 1.

7. Method for treating algae, comprising:
   (a) providing an ionic liquid, which is a conjugate of an organic base with pK$_a$ at least 6 and an acid,
   (b) providing algae,
   (c) subjecting algae to cell lysis with the ionic liquid, whereby at least two phases are formed, including a hydrophobic phase and a hydrophilic phase, and
   (d) separating the hydrophobic phase containing lipids; wherein the base has a pK$_a$ higher than 13 and the acid has a pK$_a$ higher than 1.

8. The method according to claim 1, wherein a third, solid phase is formed in step (c), which phase comprises the ionic liquid.

9. The method according to claim 8, wherein the ionic liquid-containing hydrophilic phase and/or the solid phase is reused in step (c).

10. The method according to claim 9, wherein the ionic liquid is recovered from the hydrophilic phase and/or from the solid phase by distillation before the reuse.

11. The method according to claim 1, wherein the lysis in step (c) is conducted in the presence of an alcohol.

12. The method according to claim 3, wherein the algae are provided in the form of a water suspension with water content at least 75-90 wt. %.

13. The method according to claim 1, wherein the acid is carbonic acid, substituted carbonic acid, or derivatives thereof.

14. The method according to claim 13, wherein the acid is carbonic acid and the method further comprises recovering the ionic liquid by CO$_2$ stripping.

15. Method for treating algae, comprising:
   (a) providing an ionic liquid, which is a conjugate of an organic base with pK$_a$ at least 6 and an acid,
   (b) providing algae,
   (c) subjecting algae to cell lysis with the ionic liquid, whereby at least two phases are formed, including a hydrophobic phase and a hydrophilic phase, and
   (d) separating the hydrophobic phase containing lipids; wherein step (b) comprises combining said ionic liquid and said algae to form a mixture of said ionic liquid and algae, and adding methanol so as to be included in said mixture of ionic liquid and algae.

16. The method of claim 1 which further includes:
(a) separating said hydrophobic phase from said hydrophilic phase to obtain the hydrophobic phase containing lipids and said hydrophilic phase;
(b) removing ionic liquid from said hydrophilic phase of step (d) by distillation as free acid and free base, so as to obtain recovered acid and base;
(c) forming the ionic liquid from said recovered acid and base,
(d) reusing the ionic liquid formed in step (f) from recovered acid and base in step (c).

17. The method according to claim 6, wherein the ionic liquid is formed in situ from a respective base and a respective acid.

18. The method according to claim 6, wherein the algae are provided in the form of a water suspension with water content at least 50 wt. %.

19. The method according to claim 7, wherein the ionic liquid is formed in situ from a respective base and a respective acid.

20. The method according to claim 7, wherein the algae are provided in the form of a water suspension with water content at least 50 wt. %.

21. The method according to claim 15, wherein the ionic liquid is formed in situ from a respective base and a respective acid.

22. The method according to claim 15, wherein the algae are provided in the form of a water suspension with water content at least 50 wt. %.

23. The method according to claim 15, wherein the base is selected from a list consisting of trialkyl amines, amidines, guanidines, triethylenediamine, pyridines, pyrimidines, phosphoranes and derivatives thereof.

24. The method according to claim 15, wherein a third, solid phase is formed in step (c), which phase comprises the ionic liquid.

* * * * *